United States Patent
Kipke et al.

Patent Number: 5,487,662
Date of Patent: Jan. 30, 1996

[54] DENTAL IMPRESSION TRAY FOR PHOTOCURABLE IMPRESSION MATERIAL

[75] Inventors: Cary A. Kipke, Woodbury; James G. Bentsen, North St. Paul, both of Minn.

[73] Assignee: Minnesota Mining and Manufacturing Company, St. Paul, Minn.

[21] Appl. No.: 216,148

[22] Filed: Mar. 22, 1994

[51] Int. Cl.⁶ ............ A61C 1/00; A61C 3/00; A61C 5/00; A61C 9/00

[52] U.S. Cl. ............ 433/37; 433/29; 433/215; 433/229

[58] Field of Search ............ 433/29, 37, 215, 433/214, 229; D26/2, 3, 27; 362/806, 811, 362

[56] References Cited

U.S. PATENT DOCUMENTS

| | | | |
|---|---|---|---|
| 1,084,017 | 1/1914 | Lautenburg . | |
| 3,620,778 | 11/1971 | Merrell | 106/35 |
| 4,034,476 | 7/1977 | Johnson | 32/66 |
| 4,361,528 | 11/1982 | Ginsburg et al. | 264/28 |
| 4,449,928 | 5/1984 | von Weissenfluh | 433/40 |
| 4,521,835 | 6/1985 | Meggs et al. | 362/216 X |
| 4,543,063 | 9/1985 | Cohen | 433/175 |
| 4,553,936 | 11/1985 | Wang | 433/37 |
| 4,657,959 | 4/1987 | Bryan et al. | 524/266 |
| 4,666,406 | 5/1987 | Kanca, III | 433/229 |
| 4,691,039 | 9/1987 | Aasen et al. | 556/446 |
| 4,740,159 | 4/1988 | Hamilton et al. | 433/37 |
| 4,761,136 | 8/1988 | Madhavan et al. | 433/214 |
| 4,790,752 | 12/1988 | Cheslak | 433/37 |
| 4,802,851 | 2/1989 | Rhoades | 433/29 X |
| 4,818,231 | 4/1989 | Steiner et al. | 433/215 |
| 4,858,084 | 8/1989 | Sheryll | 362/154 X |
| 4,867,680 | 9/1989 | Hare et al. | 433/37 |
| 4,867,682 | 9/1989 | Hammesfahr et al. | 433/37 |
| 4,877,854 | 10/1989 | Hattori et al. | 528/15 |
| 4,885,663 | 12/1989 | Parker | 362/32 |
| 4,888,489 | 12/1989 | Bryan | 250/504 H |
| 5,005,108 | 4/1991 | Pristash et al. | 362/31 |
| 5,030,093 | 7/1991 | Mitnick | 433/164 |
| 5,062,027 | 10/1991 | Machida et al. | 362/216 X |
| 5,066,231 | 11/1991 | Oxman et al. | 433/214 |
| 5,086,148 | 2/1992 | Jochum et al. | 528/15 |
| 5,118,290 | 6/1992 | Muller et al. | 433/48 |
| 5,136,480 | 8/1992 | Pristash et al. | 362/31 |
| 5,145,886 | 9/1992 | Oxman et al. | 522/66 |
| 5,147,204 | 9/1992 | Patten et al. | 433/229 |
| 5,155,252 | 10/1992 | Yamamoto et al. | 560/190 |
| 5,179,186 | 1/1993 | Müller et al. | 528/49 |
| 5,184,044 | 2/1993 | Thomas | 313/638 |
| 5,316,473 | 5/1994 | Hare | 433/29 |

FOREIGN PATENT DOCUMENTS

| | | |
|---|---|---|
| 0170219 | 2/1986 | European Pat. Off. . |
| 0173085 | 3/1986 | European Pat. Off. . |
| 0255286 | 2/1988 | European Pat. Off. . |
| 0269071 | 6/1988 | European Pat. Off. . |
| 0460478A2 | 12/1991 | European Pat. Off. . |
| WO95/07731 | 3/1995 | WIPO . |

OTHER PUBLICATIONS

Lumitex brochure, Lumitex, Inc., 1992.
Genesis™ brochure, The L.D. Caulk Division, Dentsply International Inc., 1988.

*Primary Examiner*—Nicholas D. Lucchesi
*Attorney, Agent, or Firm*—Gary L. Griswold; Walter N. Kirn; James D. Christoff

[57] ABSTRACT

A dental impression tray includes a self-contained light source for curing photocurable impression material. The light source is a solid state light emitter such as a light emitting diode. In one embodiment, an array of light emitting diodes is arranged along a channel of the tray. In another embodiment, a light dispersive material distributes light into the tray channel from a bank of one or more emitters.

27 Claims, 2 Drawing Sheets

DENTAL IMPRESSION TRAY FOR PHOTOCURABLE IMPRESSION MATERIAL

BACKGROUND OF THE INVENTION

1. Field of the Invention

This invention relates to a dental impression tray especially adapted for use with impression materials that cure upon exposure to light.

2. Description of the Related Art

Dental impression trays are used to hold impression material for making a model of a patient's tooth and oral tissue anatomy so that a crown, bridge, denture, veneer, restoration or the like can be made. A typical procedure involves placing a quantity of impression material in an open trough or channel of the tray and then pressing the tray onto the dental arch of the patient. The impression material is allowed to cure while in the oral cavity. The tray with the impression material is then removed from the oral cavity, and the impression material is used to prepare a positive model that replicates the selected area of the patient's arch.

Most conventional dental impression materials are made by mixing two components immediately before the impression is taken. Mixing of the components initiates a polymerization reaction that eventually causes the material to harden and cure. Consequently, as soon as the components are mixed, it is important for the dental practitioner to promptly deliver the tray to the oral cavity and accurately position the impression material relative to the selected area of the dental arch so that an accurate impression can be made.

Typically, a manufacturer of dental impression material provides recommended guidelines to the practitioner that specify both a working time and a setting point time to be followed when using the material. The working time is determined by the composition of the polymeric system and is the total time allowed for mixing the components, placing the mixed components in the tray, delivering the tray to the oral cavity and accurately seating the impression material onto desired areas of the patient's dental arch. The setting point time relates to the degree of curing of the impression material, and represents the total time that should elapse (after the components are mixed) before the tray is removed from the oral cavity in order to ensure that the impression material has cured to a degree sufficient that the impression will not be distorted as the tray is removed from contact with the dental arch.

A variety of dental impression materials are currently available that polymerize upon mixing of two components. Such materials include, for example, hydrocolloids, polysulfides, polyethers and silicones. Recommended working times and setting point times for such materials are often in the range of about 1.25 to 7 minutes and 1.5 to 10 minutes respectively.

Unfortunately, dental impression materials that begin to polymerize upon mixing are not entirely satisfactory, in that taking of the impression should be completed within a predetermined amount of time. If, for example, the procedure is interrupted by the dentist or by the patient for some unforeseen reason, the impression material may cure to such a degree that it is unusable before the procedure can be resumed. Another problem associated with such impression materials relates to the differences in recommended working times and setting point times for the variety of materials that are currently available, since a dental practitioner who has long used one type of material may fail to follow the manufacturer's recommended working time and setting point time for another material that is substituted.

In many impression materials that cure upon mixing, the length of the working time and the setting point time are determined by the amount of catalyst in the mixture. As a consequence, one who attempts to decrease the setting point time by increasing the catalyst concentration may be frustrated because the working time may also be unduly shortened. Conversely, an attempt to increase the working time may result in lengthening the setting point time by an unsatisfactory amount.

Certain impression materials that are mixed in the dental office are also unsatisfactory in instances where the mixing method (such as hand spatulation) introduces air bubbles into the mixture. Air bubbles may cause surface imperfections in the finished impression. In addition, it should be noted that mixing of the materials by hand spatulation is inherently somewhat time consuming.

It has been suggested that the use of photopolymerizable dental impression materials overcomes the disadvantages often associated with impression materials that are curable when mixed. Photopolymerizable impression materials include a photocatalyst and/or a photoinitiator that initiates polymerization of the impression material upon exposure to an appropriate wavelength of light. In the absence of such a light source, the impression material will remain substantially unpolymerized for a relatively long period of time so that the dental practitioner can ensure that the tray is accurately positioned before the impression material cures. Examples of photocurable materials are set out in U.S. Pat. Nos. 5,179,186, 5,145,886, 4,761,136, 4,543,063 and 4,740,159 and European patent applications publication nos. 0460478, 0269071, 0255286, 0173085 and 0170219.

Photopolymerizable impression materials also provide a potential advantage in instances where the tray is accurately placed in the mouth in a relatively short amount of time. In such instances, the light source can be immediately activated to begin curing of the impression material, so that the overall time necessary to complete the impressioning procedure can be reduced. By contrast, a practitioner using an impression material that immediately begins to cure upon mixing is generally unable to shorten the time necessary for completion of the impressioning procedure even when the tray is quickly placed in the oral cavity because polymerization reaction will proceed at the same rate.

However, known dental impression trays and procedures for using such trays with photopolymerizable dental impression materials are generally unsatisfactory. Some practitioners have attempted to use photopolymerizable impression material by placing the material in a transparent tray and directing a source of light through the tray and into the impression material to initiate polymerization. Such a procedure is described, for example, in U.S. Pat. No. 4,867,682.

In the past, the light source suggested for use in curing photocurable impression materials is often the same dental material curing apparatus that is commonly found in dental offices for curing adhesives, sealants and restorative materials. Such curing apparatus are described, for example, in U.S. Pat. Nos. 4,888,489 and 5,147,204 (both of which are assigned to the assignee of the present invention) and have a rigid light guide made of a bundle of optical fibers that are fused together. Unfortunately, it is difficult to use such a light guide in the oral cavity when a dental impression tray is also in place in the oral cavity, since space in the oral cavity is somewhat limited and the patient may experience discomfort in an attempt to open his or her jaws to an extent sufficient to enable the light guide to be positioned next to various regions of the tray. The practitioner should also take care to avoid bumping the tray with the light guide so that the impression is not distorted. Another disadvantage with such practice is that the hand-held light source may not be directed toward all regions of the tray, resulting in a failure of the impression material to cure in such regions.

U.S. Pat. Nos. 4,553,936 and 4,790,752 describe dental impression trays having a portal or socket for detachably receiving the light guide of dental material curing apparatus. The trays in certain embodiments of these patents have reflective surfaces or other structure to facilitate directing the light to various regions of the tray. However, such trays are disadvantageous in that the light source is relatively expensive and the light guide must be sterilized along with the tray between uses.

Another problem associated with prior methods and devices for curing photocurable impression material involves the amount of useful light energy available from conventional light sources and the resultant time necessary to obtain the satisfactory cure. It has been observed that curing times using photocurable dental impression material and conventional light sources are often relatively lengthy, resulting in a nuisance and expense to both the dental practitioner and the patient. Such relatively lengthy curing times may be due to the variation in intensity of the light that reaches various regions of the tray. In addition, incandescent lamps emit light over a broad range of wavelengths, much of which is wasted since it is not absorbed by the photoinitiator or photocatalyst.

SUMMARY OF THE INVENTION

The present invention is directed to a dental impression tray that comprises a body having a channel for receiving a quantity of photocurable dental impression material. The tray includes at least one solid state light emitter mounted on the body for curing dental impression material in the channel.

Advantageously, the solid state light emitter provides an efficient source of light and can be located closely to dental impression material in the channel. The solid state emitter is relatively small, yet provides sufficient light intensity at effective wavelengths to cure dental impression material in a relatively short amount of time. In addition, the power consumption associated with solid state emitters is relatively low and, if desired, power may be provided by an inexpensive battery connected to the tray such that a self-contained light-emitting impression tray is obtained.

DETAILED DESCRIPTION OF THE PREFERRED EMBODIMENTS

A dental impression tray according to one embodiment of the invention is designated broadly by the numeral 10 in FIGS. 1–4. The tray 10 includes a body 12 and a power source or battery pack 14 that is detachably connected to the body 12.

Figure 2:
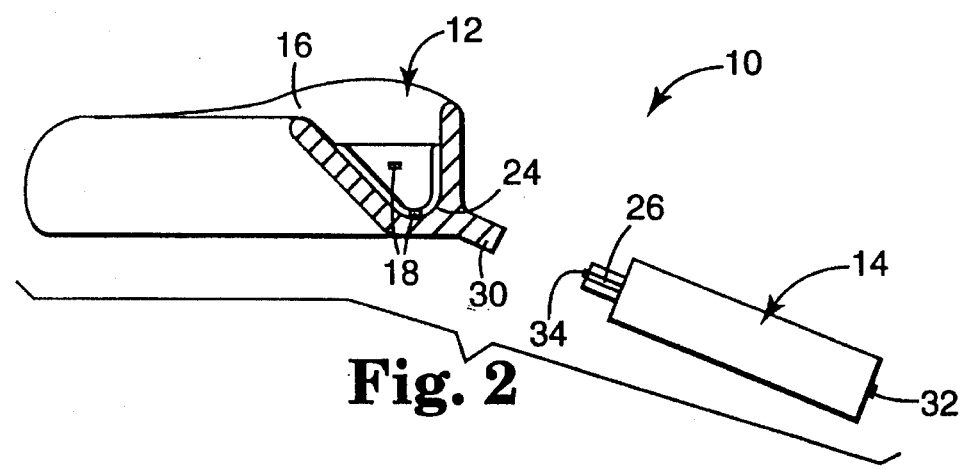
FIG. 2 is a side view in partial section of the impression tray shown in FIG. 1, except that a power source in the nature of a battery pack is shown as detached from a body of the tray.
Figure 3:
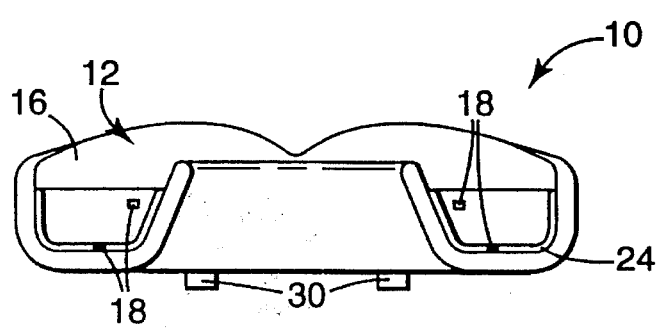
FIG. 3 is an end elevational view of the body of the tray alone that is shown in FIG. 1.

The body 12 includes an elongated channel 16 having a generally U-shaped configuration in elevational view as shown in FIGS. 2 and 3. The channel 16 is adapted to receive a quantity of photocurable dental impression material for making an impression of a patient's arch.

Figure 1:
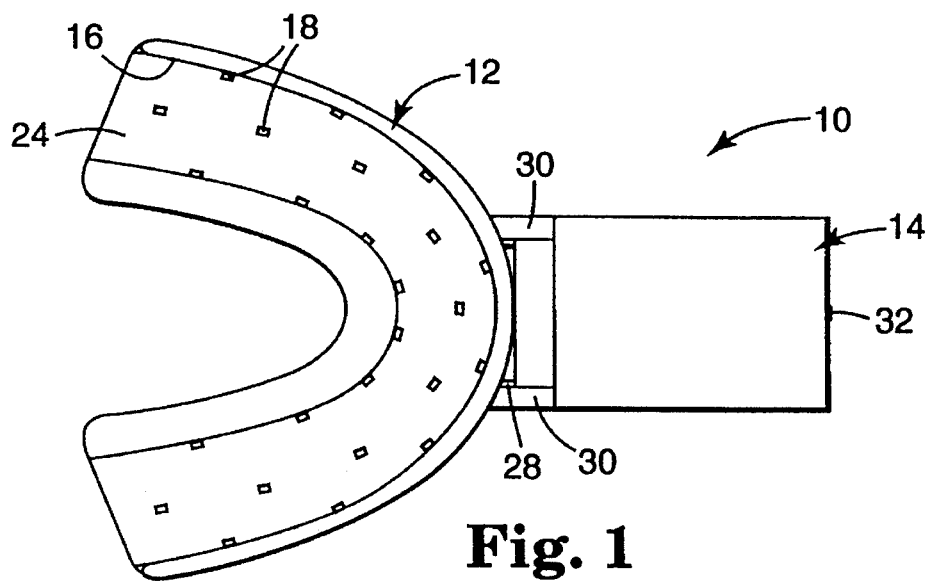
FIG. 1 is a plan view illustrating a dental impression tray in accordance with one embodiment of the present invention.

As illustrated in FIG. 1, the body 12 and the channel 16 also have a U-shaped configuration in plan view to approximately match the configuration of the patient's upper or lower dental arch. Other shapes are also possible; for example, the body may have a configuration adapted to match only a quadrant, or half of the dental arch of a patient.

A number of solid state light emitters 18 are mounted in an array that, in the embodiment shown, comprises three rows. One row is located along the center and bottom of the channel 16 in alignment with the generally U-shaped configuration of the body 12. The other two rows are positioned along sidewalls of the channel 16. Optionally, the emitters 18 may be arranged in such a fashion that additional emitters 18 are provided in areas where the channel 16 is relatively wide and contains a greater volume of impression material than other areas of the channel 16.

As used herein, the phrase "solid state light emitter" means any device that converts electric energy into electromagnetic radiation through the recombination of holes and electrons. Examples of solid state light emitters include semi-conductor light emitting diodes, semi-conductor laser diodes, polymer light emitting diodes and electroluminescent devices (i.e., devices that convert electric energy to light by a solid phosphor subjected to an alternating electric field). The light preferably has wavelengths in the visible range (i.e., from about 400 nanometers to about 700 nanometers), in the near-infrared range (i.e., such as from about 700 nanometers to about 980 nanometers), or both. A particularly preferred wavelength range is known as the therapeutic window for tissue transmission and extends from about 630 nanometers to about 980 nanometers. The wavelength of the emitted radiation is selected to provide optimum photoinitiation of dental impression material received in the channel 16, and accordingly is selected by reference to the type of photoinitiator employed in the impression material.

The light emitting diodes are p-n junction heterostructures made from semiconductor materials that are doped to result in the emission of light within a desired, preferably narrow, band of wavelengths that match the wavelength band of light that is absorbed by the photoinitiator or photocatalyst. Such heterostructures are also referred to as "optical devices" or "chips". Suitable semiconductor materials include AlGaAs for providing light in a selected wavelength band that lies in the range of about 600 to 900 nanometers, InGaAs for providing light in a selected wavelength band that lies in the range of about 900 to 980 nanometers, and AlGaInP for providing light in a selected wavelength band that lies in the range of about 560 to 650 nanometers. The selected wavelength band is determined by the choice of doping level in the fabrication of the semiconductor chip.

Light emitting diode assemblies that include semiconductor chips providing light in the abovementioned visible or near-infrared ranges are commonly sold, but are typically assembled or packaged with a relatively bulky focusing lens and a pair of wire leads. Examples of such assemblies include nos. E21, E22, E100, E102, E104 and E106 from Gilway Technical Lamp of Woburn, Mass. Preferably, however, the emitters 18 lack such lenses and leads and include only the relatively small semiconductor chips so that the overall size of the tray 10 is relatively compact and the light is emitted in many directions.

Figure 4:
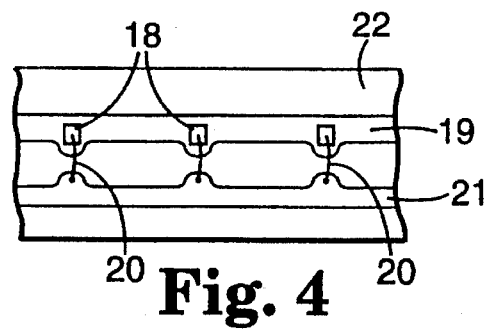
FIG. 4 is an enlarged, fragmentary, schematic plan view of the body of the tray and a number of light emitting diodes that are mounted on the body.

Electrical connections for the chips or emitters 18 are shown schematically in more detail in FIG. 4. Each emitter 18 is bonded by silver epoxy (or optionally by a solder bond) to a conductive bus 19 that is preferably made of gold. The bottom of each emitter 18 has a n-type terminal in electrical contact with the bus 19. Each emitter also has a top, p-type terminal that is electrically coupled by a small wire bond 20 to a second conductive bus 21 that is also preferably made of gold.

Three pairs of buses 19, 21 are provided for the tray 10 illustrated in FIGS. 1–3, one pair for each of the three rows of emitters 18. Each pair of buses 19, 21 is mounted on a respective ceramic substrate 22 that is, in turn, adhesively bonded to one of the sidewalls or to the bottom of the channel 16. The three substrates 22 extend in three generally parallel arcs along substantially the entire length of the curved channel 16.

The emitters 18, the buses 19, 21 and the wire bonds 20 are covered with an electrically non-conductive transparent or translucent protective polymeric coating 24 that has a smooth upper surface for contact with the dental impression material. Suitable materials for the coating 24 include clear epoxies. Ideally, the combined thickness of the emitters 18, the coating 24 and the wall of the tray defining the channel 16 is minimized in order to limit the size of the tray 10 and thus facilitate placement of the tray 10 in the limited space of the oral cavity.

The use of light emitting diodes as emitters 18 is particularly advantageous in that the diodes provide light having selected wavelengths in a relatively narrow range that optimizes initiation of the polymerization reaction. Moreover, if the selected diode emits light having wavelengths in the therapeutic window, the intensity of the light is greater than the intensity that would be provided by similar light emitting diodes operating near the center of the visible wavelength region. Light having wavelengths in the therapeutic window provides better penetration of the soft oral tissue and may provide improved curing of the impression material in gingival and sub-gingival regions in comparison to light having wavelengths near the center of the visible spectrum. Such light also penetrates the impression material more deeply because the light is scattered less than light having shorter wavelengths.

As an option, the upwardly facing surface of the body 12 adjacent the bottom of the channel 16 is covered with a reflective material (not shown) to facilitate distribution of light into the impression material in the channel 16. Suitable reflective materials include barium sulfate or magnesium oxide deposits, or metallic foils. The reflective material may be affixed to the body 12 below the substrates 22 and out of electrical contact with the buses 19, 21. The reflective material is preferably covered by the protective coating 24.

The tray 10 can be repeatedly sterilized by processes such as autoclaving or cold sterilization. The body 12 may be made of a clear or opaque plastic or metallic material. A suitable material is polycarbonate.

The battery pack 14 (FIGS. 1 and 2) includes a rectangular, protruding neck having a pair of elongated grooves 26 along opposite outer sides. One of the grooves 26 is shown in FIG. 2. The grooves 26 mate with respective, elongated tabs 28 that are located on opposing inner sides of a pair of ears 30 that extend in a rearward direction from the body 12. The tabs 28 and grooves 26 provide interlocking structure for releasably connecting the battery pack 14 to the body 12.

Although not shown in the drawings, the battery pack 14 includes one or more batteries that provide sufficient power to operate the emitters 18 for a substantial length of time. The application of an appropriate electrical current through the emitters 18 via the buses 19, 21 causes the emitters 18 to emit light energy for a repeated number of impressions. Optionally, the emitters 18 may be activated by a pulsed current to increase the temporal photon flux.

The battery pack 14 includes an on-off switch 32 for energization of the emitters 18 when desired. Preferably, the switch 32 is a momentary-type membrane switch without protruding parts that might otherwise hinder sterilization.

A pair of contacts 34 (one of which is shown in FIG. 2) is mounted on the end of the neck of the battery pack 14, and each contact is electrically connected to the battery and the switch 32. The contacts 34 engage respective contact terminals (not shown) that are mounted on the body 12 between the ears 30. One of the contact terminals is electrically connected via leads to each bus 19, while the other contact terminal is electrically connected via leads to each bus 21.

Alternatively, the battery pack 14 may include a rechargeable battery, in which case a recharging stand is also provided. The recharging stand includes interlocking structure comparable to ears 30 for releasably holding the battery pack 14 in place, and also has contact terminals for engaging contacts 34 during a recharging operation.

As another alternative, the source of power may be provided by a filtered, rectified direct voltage power supply adapted to be placed on a countertop or the like near the patient's chair. In such an instance, a pair of leads extending from the power supply are connected to a plug adapted to electrically connect to a mating receptacle mounted on and encased in part by the body 12. Such construction may be advantageous in that the weight of the battery pack 14 could be avoided.

As another option, the body 12 of the tray 10 is made in modular sections (not shown), so that the overall size of the body 12 and the channel 16 could be modified as needed. With this option, the electrical components including the emitters 18, buses 19, 21 and substrates 22 are a detachable assembly adapted for connection to the body 12. As another option, each modular section of the body 12 carry a modular section of an assembly of emitters 18, buses 19, 21 and substrates 22 that physically and electrically couple to each other as the sections of the body 12 are attached together. Such modular constructions may be useful for reducing the overall size of the tray 10 to take an impression of only a portion of one dental arch, or for enlarging the overall size of the tray 10 to enable the configuration of the channel 16 to match a relatively large dental arch that may be encountered.

Other options include the use of small solid state light detectors (not shown) that are embedded in the coating 24 at various locations along the channel 16. The light detectors monitor light flux within the channel 16, and are connected to a microcontroller that turns the emitters 18 on or off as needed in various regions of the channel 16, or alternatively varies the current level of various emitters 18 to obtain a desired light flux. As another alternative, the light detectors monitor the curing of the impression material by detecting changes in reflectance optical properties of the impression material. The reflectance changes can be the result of changes in light scattering by the polymerized material and/or by optical absorption by the photocatalyst or photoinitiator. The detectors are used to alter or interrupt the current to some or all of the emitters 18, and/or to activate an audible alarm that signals that polymerization is complete.

Polymer light emitting diodes may provide advantages in certain applications. The polymer material can be provided in a thin film that readily conforms to the configuration of the tray channel.

Figure 5:
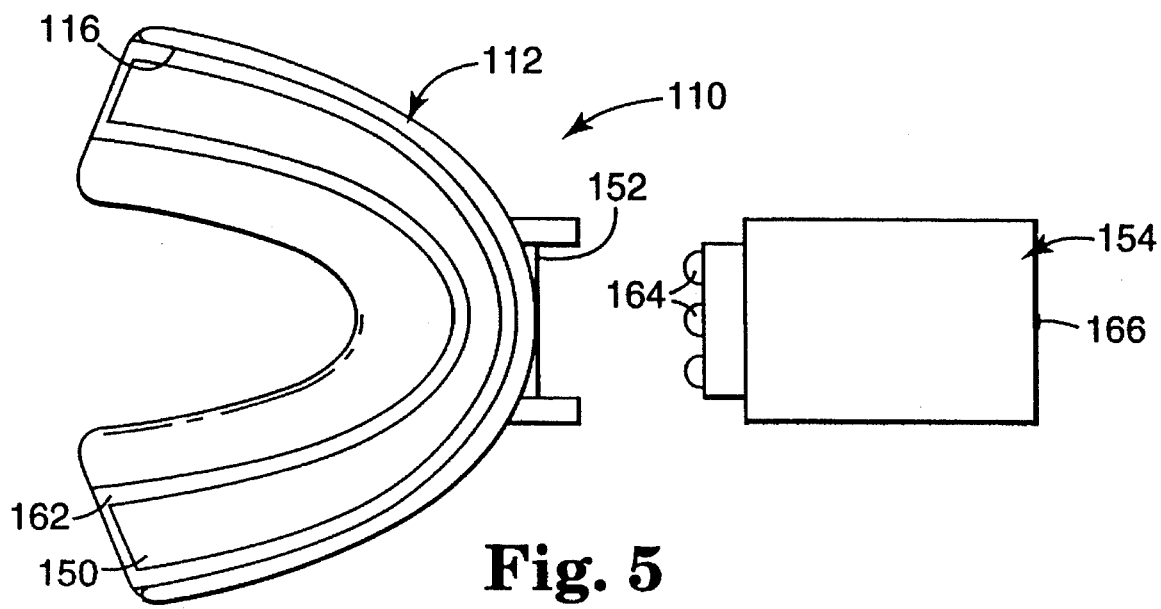
FIG. 5 is a plan view of a dental impression tray in accordance with another embodiment of the invention, wherein a battery pack is shown as detached from a body of the tray.
Figure 6:
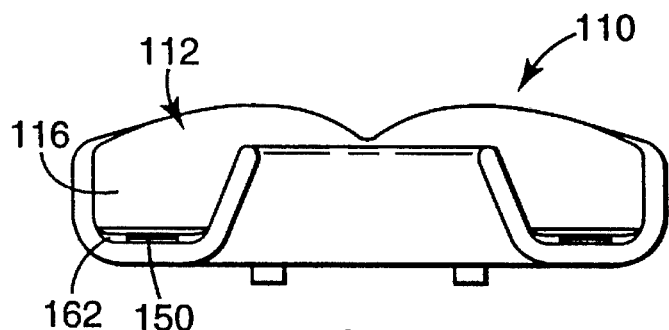
FIG. 6 is an end elevational view of the body of the tray that is depicted in FIG. 5.
Figure 7:
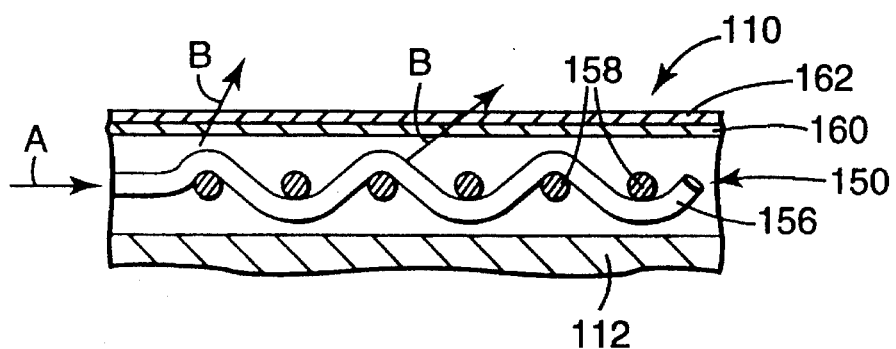
FIG. 7 is an enlarged, fragmentary, side cross-sectional schematic view of the tray illustrated in FIGS. 5–6, depicting among other things an internal light dispersive material.

Another embodiment of the invention is illustrated in FIGS. 5–7, and concerns a tray 110 having a body 112 with a channel 116 for receiving a quantity of impression material. Except for the specific features mentioned below, the body 112 is essentially identical to the body 12 described in connection with FIGS. 1–4 and as such a detailed description of the body 112 shall not be repeated.

The tray 110 includes a light dispersive material 150 having an elongated, U-shaped configuration matching the shape of the tray channel 116. The light dispersive material 150 includes a bank 152 of receptors that receive light from a detachable combination light source and battery pack 154. The material 150 distributes light in directions throughout the tray channel 116, and directs light into the channel 116 for curing dental impression material placed therein.

A suitable light dispersive material 150 is a light-emitting panel such as is available from Lumitex of Strongsville, Ohio. A schematic illustration of such a panel is shown in enlarged form in FIG. 7, wherein plastic optical fibers 156 (only one shown) are interwoven in transverse relation to fill fibers 158.

Each of the optical fibers 156 has structure along its length to enable a portion of the light traveling along the fiber 156 to be emitted from the sides of the fiber and through its cladding. The structure may be a disruption, scratch, internal reflective surface, or bend. In FIG. 7, the fibers 156 are provided with bends. Some of the light traveling in the fiber 156 in the direction of the arrow marked "A" is internally reflected and continues its travel within the fiber 156. However, a portion of the light traveling within the fiber 156 is emitted through the sides of the fiber 156 as illustrated by the arrows marked "B" in areas where the fiber 156 is bent as it passes around fill fibers 158.

The fibers 156, 158 can be molded or contoured to the desired geometry of the tray body. The fibers 156, 158 are covered by a diffuser layer 160 to facilitate even distribution of light in the channel 116. Further information regarding the fibers 156, 158 and the diffuser layer 160 is set out in U.S. Pat. Nos. 5,136,480, 5,005,108 and 4,885,663 and European patent Application No. 93.116755.5, the disclosures of which are expressly incorporated by reference herein. As an option, the diffuser layer 160 may be covered with a clear protective coating 162 similar to the coating 24 described above.

The combination light source and battery pack 154 includes a rectangular, protruding neck that carries a bank of solid state light emitters 164. The emitters 164 are preferably light emitting diodes, but in this instance may include the protective lenses and leads that are normally provided with such diodes. Suitable diodes include the diodes identified above from Gilway Technical Lamp.

The bank of emitters 164 are optically coupled to the bank 152 of optical receptors mounted on the body 112 when the combination light source and battery pack 154 is connected to the tray body 112. As a consequence, light from the emitters 164 is distributed to the light dispersive material 150 along the length of the tray body 112 and into the channel 116.

The combination light source and battery pack 154 includes an alkaline or rechargeable battery similar to the batteries mentioned above, and also includes a membrane switch 166 similar to the membrane switch 32. The neck of the combination light source and battery pack 154 includes grooves similar to the grooves 26 to provide a releasable physical interlocking connection between the combination light source and battery pack 154 and the tray body 112.

Alternate constructions include the use of a plug (not shown) having light emitters similar to emitters 164, wherein the plug is adapted to optically and physically interconnect with the body 112 in the manner similar to that shown in FIG. 5 and described above. However, the plug is connected to a pair of leads that are coupled to a remote filtered, rectified direct current power source adapted for placement on a countertop or other structure near the patient's chair.

As can be appreciated, mounting of the emitters 18, 164 on the body 12, 112 enables the light source to be positioned in close proximity to the impression material and the need for a remote light source is avoided. The invention provides the potential to deliver light of increased intensity while improving in many instances the mobility, size and perhaps overall cost of the light curing impression tray and any associated devices. Use of light emitting diodes may reduce setting time requirements of the impression material due to increased luminous intensity and narrowed wavelength band.

We claim:

1. A dental impression tray comprising:

a body having a channel for receiving a quantity of photocurable dental impression material; and at least one solid state light emitter mounted on said body for curing dental impression material in said channel, wherein said at least one solid state light emitter emits light having a wavelength in the range of about 630 to 980 nanometers.

2. The dental impression tray of claim 1, wherein said tray includes a battery holder releasably connected to said body.

3. The dental impression tray of claim 1, wherein said emitter is a light emitting diode.

4. The dental impression tray of claim 1, wherein said tray includes at least one optical fiber located in said channel and optically connected to at least one emitter.

5. The dental impression tray of claim 4, wherein said at least one optical fiber has structure along its length to enable emission of light through sides of such fiber.

6. The dental impression tray of claim 1, wherein said tray includes a woven layer of optical fibers located in said channel and optically coupled to said at least one emitter, and wherein each optical fiber has structure along its length to enable emission of light through sides of such fiber.

7. The dental impression tray of claim 1, wherein said tray includes at least one light detector.

8. The dental impression tray of claim 1, wherein said channel includes a bottom and at least one sidewall, and wherein said at least one solid state light emitter includes an array of light emitting diodes at least some of which are positioned along said at least one sidewall.

9. The dental impression tray of claim 1, wherein said at least one solid state light emitter includes an array of light emitting diodes that each lack a corresponding, discrete focusing lens.

10. A dental impression tray comprising:

a body having a channel for receiving a quantity of photocurable dental impression material;

at least one light emitting diode mounted on said body for curing dental impression material in said channel, each of said at least one light emitting diode lacking a corresponding, discrete focusing lens; and a layer of polymeric material extending across the body and covering each light emitting diode.

11. The dental impression tray of claim 10, wherein said at least one light emitting diode emits light having a wavelength in the range of about 630 to 980 nanometers.

12. The dental impression tray of claim 10, wherein said tray includes a battery holder releasably connected to said body.

13. The dental impression tray of claim 10, wherein said channel has sidewalls and a bottom, and wherein said at least one light emitting diode includes an array of light emitting diodes at least some of which are positioned along said sidewalls.

14. The dental impression tray of claim 10, including means to vary the light flux in various regions of the channel.

15. The dental impression tray of claim 14, wherein said means includes at least one light detector connected to said body.

16. The dental impression tray of claim 15, wherein said at least one detector is embedded in said layer of polymeric material.

17. The dental impression tray of claim 10, including means to vary the current to said at least one light emitting diode.

18. The dental impression tray of claim 17, wherein said means includes at least one light detector connected to said body.

19. The dental impression tray of claim 10, wherein said tray includes at least one light detector.

20. A dental impression tray comprising:

a body having a channel for receiving a quantity of photocurable dental impression material;

a source of light for curing dental impression material in the channel; and at least one light detector connected to said body.

21. The dental impression tray of claim 20, wherein said at least one light detector monitors light flux in said channel, and wherein said dental impression tray includes a controller connected to said at least one light detector and said source of light.

22. The dental impression tray of claim 21, wherein said controller varies the current to said source of light.

23. The dental impression tray of claim 21, wherein said controller turns said source of light on and off.

24. The dental impression tray of claim 20, wherein said at least one light detector senses changes in reflective optical properties of dental impression material received in said channel.

25. A method of curing dental impression material comprising the steps of:

placing a quantity of dental impression material in an impression tray;

directing light toward the impression material in the tray;

sensing reflectance optical properties of the impression material as the impression material cures; and changing the amount of light flux directed toward the impression material in response to one or more changes in the sensed reflectance optical properties.

26. The method of claim 25, wherein said step of changing the amount of light flux includes the step of interrupting the light flux.

27. A method of curing dental impression material comprising the steps of:

placing a quantity of dental impression material in an impression tray;

directing light toward the impression material in the tray;

sensing reflectance optical properties of the impression material as the impression material cures; and activating an alarm in response to one or more changes in the sensed reflectance optical properties to thereby signal that polymerization is substantially complete.

* * * * *